(12) United States Patent
Aroussi et al.

(10) Patent No.: US 6,762,827 B2
(45) Date of Patent: Jul. 13, 2004

(54) PLANAR LIGHT SHEET PROBES

(75) Inventors: Abdelwahab Aroussi, Nottingham (GB); Mohamed Menacer, Nottingham (GB)

(73) Assignee: The University of Nottingham, Nottingham (GB)

(*) Notice: Subject to any disclaimer, the term of this patent is extended or adjusted under 35 U.S.C. 154(b) by 0 days.

(21) Appl. No.: 10/286,623

(22) Filed: Nov. 1, 2002

(65) Prior Publication Data

US 2003/0133096 A1 Jul. 17, 2003

Related U.S. Application Data

(63) Continuation of application No. PCT/GB01/01860, filed on Apr. 27, 2001.

(30) Foreign Application Priority Data

Apr. 27, 2000 (GB) .............................................. 0010123

(51) Int. Cl.[7] .................................................. G01P 3/36
(52) U.S. Cl. ....................................... 356/28; 356/28.5
(58) Field of Search ................ 356/28, 28.5, 3.01–4.01

(56) References Cited

U.S. PATENT DOCUMENTS 5,202,558 A    4/1993  Barker
5,669,871 A *  9/1997  Sakiyama
5,883,707 A    3/1999  Arndt et al.
6,522,444 B2 * 2/2003  Mandella et al.

FOREIGN PATENT DOCUMENTS

| EP | 0394602 | 10/1990 |
|---|---|---|
| GB | 1545699 | 5/1979 |
| GB | 2213018 | 8/1989 |
| GB | 2337107 | 11/1999 |
| WO | 93/19376 | 9/1993 |
| WO | 95/33999 | 12/1995 |
| WO | 97/12210 | 4/1997 |

* cited by examiner

Primary Examiner—Stephen C. Buczinski
(74) Attorney, Agent, or Firm—Baker Botts L.L.P.

(57) ABSTRACT

An optical endoscopic fluid flow measurement probe assembly is disclosed having a user end and a distal end. The distal end having a light sheet generator and at least one reflected light acquirer, and the endoscope is provided with transmission means to transmit information away from the distal end. The light sheet generator is adapted in use to generate a sheet of light and the light acquirer being adapted to image light reflected from the light sheet, the light sheet generator and light acquirer being provided in the same endoscope.

27 Claims, 12 Drawing Sheets

PLANAR LIGHT SHEET PROBES

This is a continuation of application No. PCT/GB01/01860 filed Apr. 27, 2001.

The present invention relates to an optical probe adapted for use in an enclosed space, for example, a cavity to allow measurement of features such as flow rate, particle size and concentration of substances contained in the space. It is especially, but not exclusively, concerned with PIV. It is concerned with planar light sheet anemometers (PLSA), especially with miniature PLSA's.

Conventional cavity inspection devices (or devices for use in confined spaces) have allowed images to be taken/the cavity to be visualised and include endoscopes having a number of prisms and mirrors which conduct white light from a source into a cavity. The prior art endoscopes allow the user to see what is in the cavity with the naked eye or can be used in combination with a camera allowing visualisation of the cavity on a screen or a photograph.

Conventional fluid flow analysis systems such as Laser Doppler Anemometers (LDA), Particle Image Velocimeters (PIV) and Phase Doppler Anemometers (PDA) are large and when it is desired to obtain flow information in a confined space are incapable of obtaining a wide enough range of information sought, and are practically impossible to use due to the lack of optical access available in enclosed cavities (e.g. in the bearing chamber of an aero-engine).

It would therefore be beneficial in a wide variety of fields, including engineering and medicine, to have a probe system which may or may not allow the visualisation of the inside of an enclosed cavity, but more importantly allows measurements to be taken relating to the contents of the cavity, for example for a fluid-containing cavity, the particle velocity, the particle size, and particle concentration, of the fluid in the cavity.

The present invention originated from work in the field of Particle Imaging Velocimetry (PIV). Particle Image Velocimetry (PIV) benefited from the development of LDV (Laser Doppler Velocimetry) and constitutes an answer to the need for Whole Field measurements. It was developed in the late 1970's, was practically implemented in the early 1980's, and its use started to spread in the late 1980's. It is now a developed technique. The advantages of this type of measurement system are found in many domains: when using intermittent facilities flowfields may be measured without assuming perfect repeatability of testing conditions; in many instances testing times are much shorter than with other methods of flow/fluid measurement; and these techniques allow the access to quantities that were otherwise impossible to determine such as instantaneous vorticity fields. The technique typically images a particle at two different times and establishes the velocity of the particle by evaluating the images to establish how far the particle has travelled in a known time.

Particle Image Velocimetry and Laser Induced Fluorescence (LIF) are based, like Laser Doppler Velocimetry, on the measurement of the velocity of tracer particles carried by the fluid. However, rather than concentrating light in a small probe volume (as in LDV), a complete plane of the flow under investigation is illuminated in PIV and LIF. This is performed by creating a narrow light sheet which is spread over the region of interest, the sheet illuminating an isolated 2-D plane of interest. Tracer particles are therefore made visible and images of the illuminated particles are recorded. These recordings will typically either contain successive images of single tracers in time or successive frames of instantaneous images of the whole flowfield. The displacement of the tracer will then be determined through the analysis of these records.

PIV systems are known for providing information on a fluid in a confined space which have a first probe which comprises an emitter optically coupled to a laser and designed to emit a sheet of laser light, and a second probe, spaced apart from the first probe, and comprising a detector/receiver designed to detect scattered laser light and provide signals to a computer. The spacing between the emitter and the detector needs to be accurately controlled, as does their relative angular orientation and relative position.

Laser-induced fluorescence (LIF) imaging is another imaging technique which uses a sheet of light. It relies on the quantum nature of molecules and atoms, whereby energy transitions can only occur between certain quantized energy states. A diatomic molecule can have several modes of quantum energy. The three relevant to LIF Studies are electronic, vibrational and rotational. The first mode, the electronic state, is usually denoted by letter, with X being the lowest (ground) electronic state, A being the first excited state, B the second, etc. The molecule also has vibrational energy, denoted by the vibrational quantum number v, having integer values starting with 0. The third energy state is the rotational energy, denoted by the rotational quantum number J. Only certain energy transitions are allowed by the selection rules of quantum physics. A molecule in a low energy state can only be optically pumped up to a higher energy state by interaction with a photon of energy exactly equal to the energy difference between allowed energy states of the molecule, and an excited molecule can only relax by giving up a quantum of energy equal to the difference between allowed energy states, either by emission of a photon, or by collision with a neighbouring molecule.

Laser-induced fluorescence takes advantage of this phenomenon by optically exciting a species with photons of a frequency matching an allowable level difference of the species being probed. It should be noted that different species tend to have different energy transitions, so it is generally possible to chose a transition for a given species that is well isolated from possible transitions of other species that may be present. The resulting fluorescence caused as excited molecules relax by photon emission can be collected and analysed to determine local species concentration and/or temperature.

Laser-induced fluorescence utilises a sheet of laser light generated by a tunable laser source to illuminate a two dimensional plane through the sample, and uses a sensitive intensified CCD camera arranged at 90° to the sheet of light to image the resulting fluorescence from the illuminated area. The processing of the acquired images is similar to PIV except for the additional filters and detectors for phase separation. There are several variations of the principle; namely LIF, PLIF (Planar Laser Induced Fluorescence), MLIF (Mixing Measurements using Laser Induced Fluorescence) etc.

In some PIV/LIF measurements it is necessary to move the sheet of light, and also move the detector in a corresponding manner so as to ensure optimum detection for the new position of the sheet of light. Careful alignment of the emitter and detector at their second (and subsequent) positions is also important, but critical to the measurement process.

When, for example, measuring lubricant (oil) parameters in a working engine (e.g. a working test-bed aeroplane engine) such as a turbine jet, it is necessary to put two probes (emitter and detector) into the fluid flow.

This disrupts the flow away from what it is in use, without the probes. Of course, the size of the probes is kept small in the prior art, and the tests are performed with the probes in different positions to see how that effects the results.

According to a first aspect of the invention we provide an endoscopic optical fluid measurement probe assembly comprising an endoscope having a user end and a distal end, the distal end having a light emitter and a reflected light acquirer; and the endoscope being provided with transmission means to transmit information away from the distal end.

Thus, a single probe both emits light and detects light reflected by the fluid: both serves as emitter and data acquirer. This reduces the disruption in comparison with traditional two-probe PLSA systems. A single probe can also get into smaller spaces than can two probes and yield minimal intrusion.

Preferably the probe is adapted to emit laser light. Preferably the probe comprises a PIV probe or a LIF probe and the light emitter may comprise a light sheet producer adapted in use to produce a sheet of light. The probe may comprise one of: a PIV probe, a LIF probe, a stereoscopic 3-D PIV device, or any Planar Light Sheet Anemometer (PLSA). At present white light techniques do not provide as good results as laser light sheets, and laser light sheets is an important feature of many embodiments of the invention, but a non-laser light sheet may be envisaged.

Preferably the endoscope comprises a light-transmitting channel, such as a crystal, fibre optic, or fibre optic bundle, extending along its length and optically coupled to the light emitter. Preferably the optical channel, e.g. fibre optic, is adapted to be optically coupled to a laser, for example when a Continuous wave laser is providing the light source or when a low energy pulsed laser is used.

Preferably the light acquirer is optically coupled to image transmission optics adapted to transmit an optical image or signal detected by the light acquirer away from the distal end, and preferably to the user end of the probe. The transmission optics preferably comprise one or more of lenses, prisms, and mirrors, and preferably comprises at least one lens, and at least two elements of (i) mirrors elements, or (ii) prism elements. There may be at least two mirrors, and/or at least two prisms, or at least one of each.

The image transmission optics is arranged to transmit the acquired image to a camera or other imaging device provided outside of the confined space into which the distal end of the endoscopic probe has been inserted. Of course, if cameras became small enough to be introduced into confined spaces, and if they become robust enough to survive and operate in the environmental conditions to which they are exposed in use, the camera itself may be provided at the distal end of the endoscopic probe. For example a small CCD camera may be provided at the distal end of the probe, and image signals may be exported from the distal end (e.g. electrical signals or a wireless e.m. transmission). However, using optical components and transmitting the image itself away from the distal end to a camera remote from the distal end is preferred at present since the probe can be kept smaller/the mirrors/lenses/prisms can cope with more extreme environments.

There may be a first optical element with a reflective surface inclined at generally 45° to a reflective surface of a second optical element. The light acquirer may have a pair of optical elements (e.g. mirrors or prisms) with reflective surfaces extending generally parallel to each other.

The light acquirer may have an optical element having a reflective surface, and the light emitter may have an optical element having a reflective surface, and the reflective surfaces may be inclined relative to each other so as to create a light output in a first plane that is substantially normal to the line of sight of the optical element of the light acquirer. It will be appreciated that the line of sight of the light acquirer is the line that is reflected up the endoscope, in use of the endoscope. The reflective surfaces of the light acquirer and light emitter may be inclined at an angle between 0° to 90° to each other, or at another angle that may be by 90°, or may not be 90°.

The endoscope may have an elongated body, preferably tubular, and preferably provided with an extension, arm, or foot at or towards its distal end. The foot may extend away form the body, possibly at about 90° to the body.

The light emitter may include an offset arrangement such that the light emitted in use passes transversely across the elongate body, with the light acquirer preferably being provided in the body. Alternatively, the light emitted by the light emitter may be arranged to propagate generally parallel to the elongate direction of the body.

The light acquirer preferably has a movable, preferably angularly movable, reflector. The reflector may be provided on a carrier. The carrier is preferably angularly movable about a first axis. The reflector is in some embodiments preferably angularly movable relative to a carrier about a second, different, axis.

For stereoscopic measurements an embodiment of the endoscopic probe has a first and a second arm or foot, typically at or towards its distal end, and each arm/foot has an image acquirer. In the arrangement of a preferred embodiment the image acquirer of the first arm acquires an image from one side of the sheet of light and the image acquirer of the second arm acquires an image from the other side of the sheet of light. This allows the out-of-plane velocity of particles to be established (velocity transverse (e.g. perpendicular) to the plane of the sheet of light).

Although any light source could be used, a laser is usually the most preferred source to produce a narrow and intense light sheet. Laser beams constitute well-collimated sources of intense light and they can very easily be transferred into a sheet using cylindrical lenses or scanning mirrors. Continuous or pulsed laser may be used depending on the technique to be applied. Argon lasers are good choices of continuos light and Ruby or ND-Yag lasers are chosen when a pulsed source is needed. The latter nowadays replaces more and more Ruby lasers since it allows easier focusing of a camera.

The energy available is best used by creating a very narrow light sheet. This may be accomplished by adding spherical positive lenses to the optical system to reduce the divergence of the laser beam.

The continuous wave or low energy pulsed light sheet may be transmitted into a confined space (e.g. a cavity) using fibre optics, alternatively (for example where the light source is a high energy pulsed laser) the beam can simply be directed into the cavity/combined space via mirrors, lenses and prisms.

The, or each, light acquirer may have a line of sight that is substantially perpendicular to the plane in which, in use, a sheet of light will be created by the light sheet producer. This gives the strongest reflected signals (reflected off particles in the fluid being measured), and may make the mathematics of the analysis software more straightforward.

The transmission optics may direct an image, or optical signals, into a camera, a sensor, or an array of sensors, which may comprise part of the probe assembly, or the probe assembly may not include them and instead be adapted to be coupled to them. The camera may be a photographic film camera. The camera may alternatively be a charge coupled device camera. The camera may communicate with a time delay and sequence generator to allow it to record images at predetermined intervals. The assembly preferably further includes means to analyse the recorded images. The means of analysis of the recorded image(s) is preferably a computer and appropriate software, to which signals from the camera (or sensor or sensor array) are fed.

The present invention according to another aspect comprises a method of determining a parameter associated with a fluid in a restricted space and/or a hostile environment, comprising using an endoscopic optical probe having an elongated length and provided with an optical light emitting element towards its distal end and provided with an optical light acquiring element towards its distal end, the probe being adapted to emit light via the light emitting element and collect light, via the light acquiring element, that has been emitted by the emitting element and interacted with the fluid; and transferring acquired light, or other signals, away from the distal end, for example along the endoscopic probe to a remote sensor, remote from the distal end of the endoscopic probe; and processing signals produced by the remote sensor to evaluate a parameter of the fluid.

Preferably the processing comprises applying one of the following techniques to the signals: PIV; LIF, PLIF, MLIF, stereoscopic PIV, or any PLSA technique.

Preferably, the method comprises determining at least one of the following in an environment that is hostile or conventionally inaccessible; such as an engine bearing (preferably an aircraft engine bearing): fluid flow; particle analysis; and temperature.

The present invention further provides a method of determining a parameter associated with a fluid (such as fluid velocity, temperature, or particle size and concentration) comprising the steps of:- producing a first light sheet;

transmitting the first light sheet into the fluid using an endoscope;

recording the image illuminated by the first light sheet using an image acquirer provided on the same endoscope.

Preferably the method further comprises:

producing a second light sheet;

transmitting the second light sheet into the fluid using the endoscope;

recording the image illuminated by the second light sheet;

analysing the images illuminated by the first and second light sheet and determining the required parameter.

The means to produce the light sheet is preferably a laser light source with optics. The preferred light source is a laser. The light sheet may be transmitted into the fluid, or confined space or cavity, using fibre optics or alternatively where the light source is a laser fibre optics may not be necessary: the laser beam can simply be transmitted into the cavity.

The fluid may have particles in it, for example tracer particles, which may be deliberately introduced into the fluid. The shutter of the camera may be opened for a sufficient time, synchronised with pulses of the laser, to produce snapshots separated in time. Particles may therefore be present in two images, showing the position of the particle each time of firing the laser.

It may be important that light is intense enough for the pulse duration to be as short as possible to avoid any blurring of the image of the tracer particles, and that the film used in the camera (if it has a film) is sufficiently sensitive for the wavelength of the laser. In most cases, a pulsed laser is used, but for relatively low speed flows (less than 10 m/s) it is possible to use a continuous laser such as an Argon laser together with a mechanical or opto-electronical shutter to generate the required pulses.

In most cases, the particles should be small enough to follow the flow of fluid in the cavity or other confined space (e.g. tube). They will therefore scatter a small amount of light. Furthermore, this light may conveniently be collected at 90 degrees to the incoming illuminating light.

The photographic camera can be replaced with a CCD (charge coupled device) camera. The advantage of CCD cameras is the possibility of on-line processing of the images of the flow. The disadvantage is the low resolution of the camera presently available, which limits the size of the interrogation area. However, resolution may well improve in future CCD cameras.

High-speed image capture and data transfer to the computer are accomplished by the use of hardware processors or by software. The latter lends itself better for flexibility, accuracy, new developments and other novel analysis schemes preferred by users. Real time, or nearly real time, analysis may be possible.

According to an other aspect the invention comprises performing LSV, PIV, LIF, PLSA, stereoscopic 3-D PIV, or other optical fluid flow analytic techniques using the same endoscope to emit light and to detect reflected light.

According to another aspect the invention comprises the use of an endoscopic probe assembly in accordance with the first aspect of the invention in the performance of a fluid flow analytical technique.

According to another aspect of the invention, we provide a fluid analyser system comprising a probe in accordance with the first aspect of the invention coupled to a laser or other light source, and coupled to at least one camera, or two cameras, or to another detector(s).

Preferably the system comprises a control device, such as a computer or microprocessor which in use controls the operation of the laser and receives signals from the detector. Preferably the control device is also adapted, in use, to control the movement of the endoscope.

It will also be appreciated that an endoscopic probe having optical light emitting and light capturing elements at its distal end and light transmission means along its elongate length allows the provision of the sensitive camera/detector, and sensitive and bulky laser and power supply and control, remote from the distal, inspection, end which can therefore be placed in hostile environments. So long as the light emitting and capturing elements are capable of withstanding the conditions, and the body of the endoscope itself can withstand the conditions, the distal end can experience conditions that would destroy the camera/detector.

Since making the invention we have become aware from a UK Patent Office Search of GB 1 545 699 which discloses a probe, but not a light sheet and is not PIV, and does not handle images; U.S. Pat. No. 5,202,558 which does not relate to light sheets and is not a pulsed system, and is not PIV; WO 93/19376 which is not a miniature probe, not PIV, has no light sheet emitted, and is not imaging in a 2-D sheet; WO 95/33999 which deals with beams not sheets, is not a single probe; and does not image particles; EP 0 394 602 which is not a miniature probe and does not have the same single probe transmit and receive light and detected images; GB 2 213 018 which has no light sheet, does not image, and is not PIV; and GB 2 339 107 which has two beams, has no sheet of light, does not image particles, and is not PIV.

Embodiments of the present invention will now be described by using an example with reference to the drawings of which:

Figure 1:
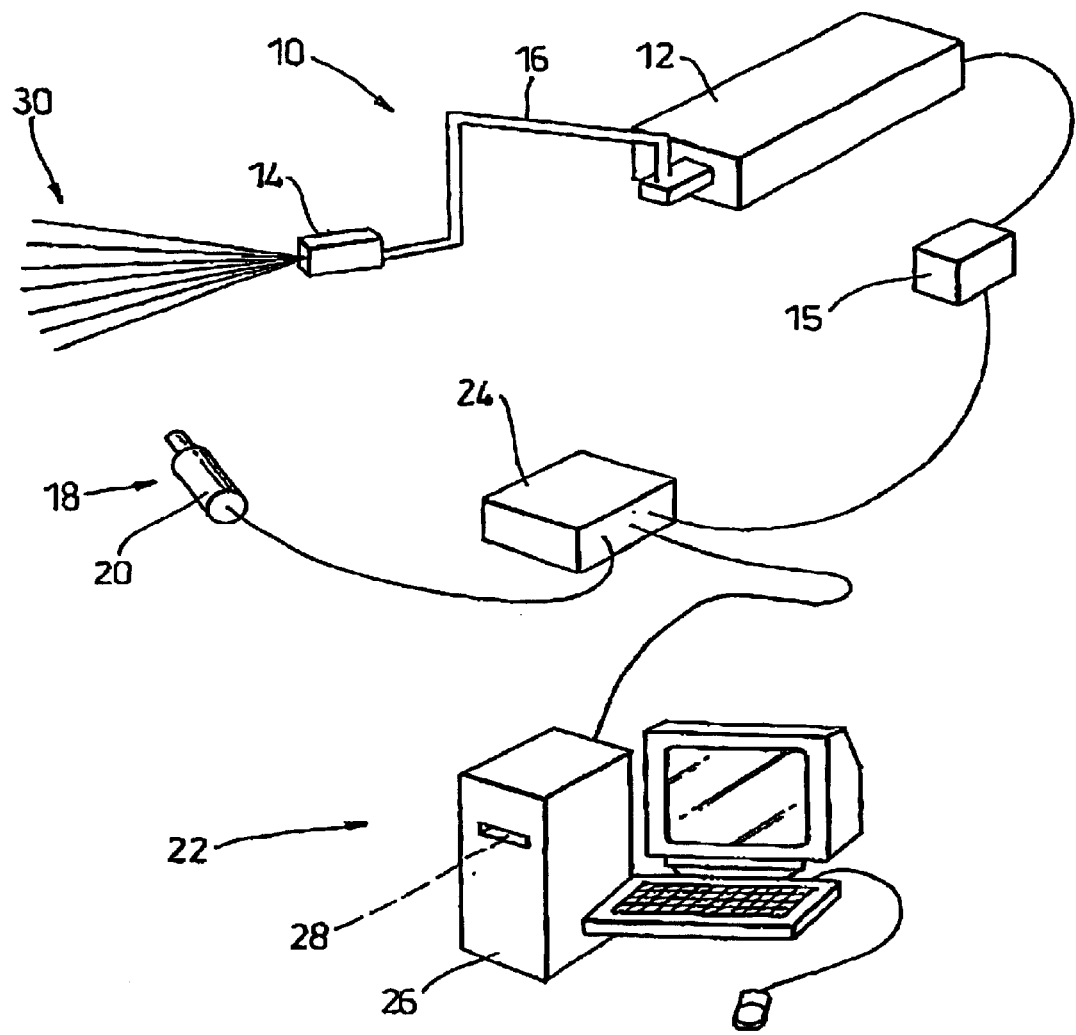
FIG. 1 shows a prior art PIV system.

FIG. 1 shows a prior art PIV system comprising a light source 10 (laser 12, light sheet former 14, laser power supply 15, and communicating optics 16), an image recording medium 18 (CCD camera 20), a programmable time delay and sequence generator 22 (synchroniser 24 and computer 26), and image acquisition/analysis software 28 (on computer 26). The laser sheet of light (referenced 30) and the acquisition of signals from the camera 20 are synchronised by the synchroniser 24 to isolate 2-D planes. The image captured by the camera 20 is analysed by computer software in a known manner. The light sheet former 14 is a bulky box, and the camera 20 is bulky. Their relative position and orientation needs to be carefully controlled. Having the camera and the light sheet former in a hostile environment is difficult: the camera cannot tolerate too extreme conditions. Getting the camera and the light sheet former into confined spaces is impossible: they are too large.

Figure 2:
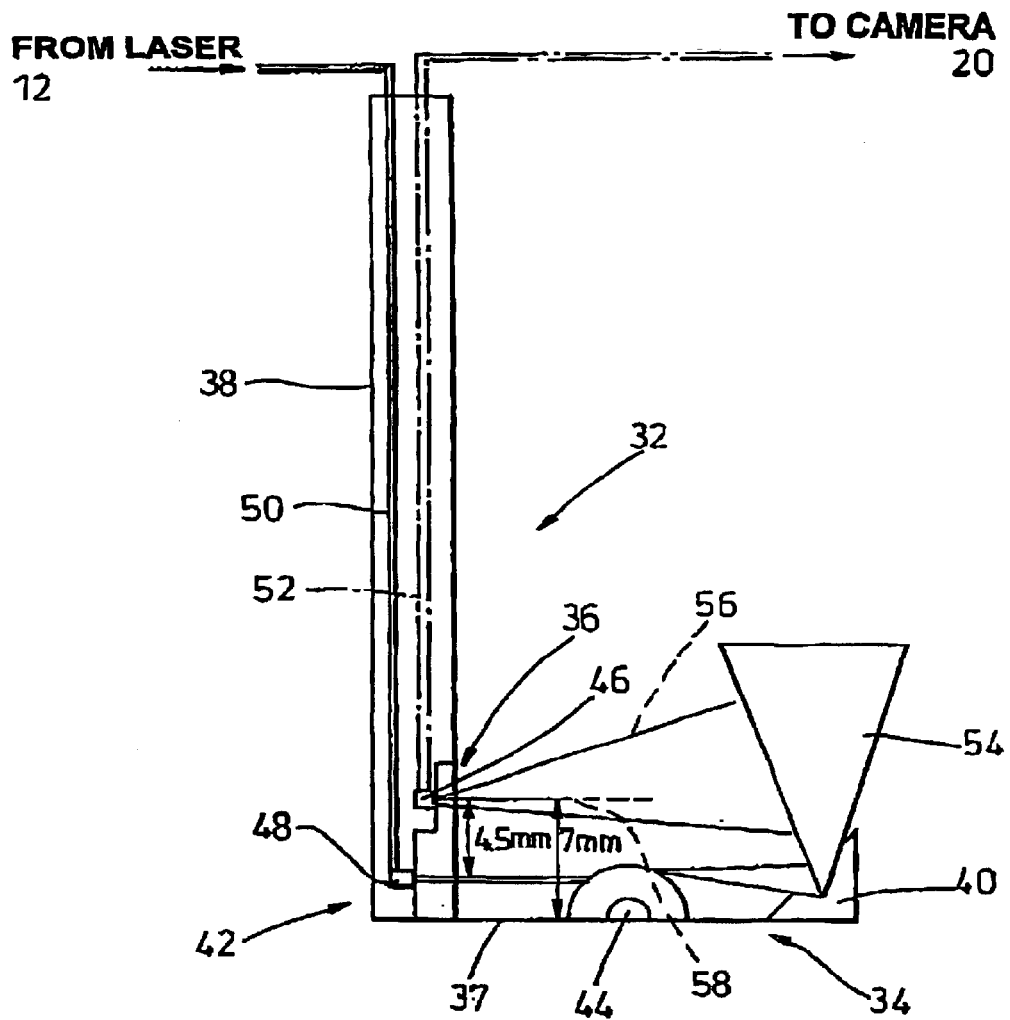
FIG. 2 shows a cross section of a first probe design.

FIG. 2 shows an endoscopic PIV probe 32 which has both light emission and data acquisition, and which can get into confined spaces and hostile environments. The probe 32 has light emitting optic 34 and light capturing optics 36. The probe 32 has a borescope, or shaft, 38 carrying a mirror 40 at its distal end 42. The mirror 40 is in fixed relationship with the shaft 38 (but in other embodiments could movable relative to the shaft, with the provision of mirror-movement means). The mirror 42 is inclined at 45° to the direction of the shaft 38 (and at 45° to a base portion 37 of the probe 32. Also carried at the distal end 42 is light sheet forming optics 44. This is a known light sheet generation device.

The borescope 38 has a viewing window 46 spaced from its distal end 42, and a light output unit 48 disposed along the length of the borescope between the viewing window 46 and the end most part of the scope 38. A fibre optic 50 extends along the shaft of the borescope and is coupled to the light output unit 48 or extended to the light sheet forming optics 44. The light capturing optics 36 is in this example a series of prisms, lenses and mirrors adapted to transmit a captured light signal up the borescope to a detector/camera (referenced 20) associated with the near (near to user) end of the endoscope. The transmission path of captured light is referenced 52. It will be appreciated that the light emitting optics 34 comprises the fibre optic 50, the light output unit 48, the light sheet forming optics 44, and the mirror 40. The light capturing optics 46 are the lenses, mirrors, and prisms that take light from the window 46 to the camera 20 (or other detector or detector array).

We prefer to use a laser having a wavelength of 532 nm, and typically lasers in the visible range, for example of the order of 500 to 700 nm may be preferred. We prefer to use light with a wavelength that is comparable with the expected size of particles in the fluid. A Mie theory scattering method may be used.

It will be appreciated that in FIG. 2 the sheet of light, referenced 54, is shown schematically and is really in a "vertical" plane extending out of the page, perpendicular to the page, and that the window 46 is adapted to receive light from a "horizontal" plane (schematically shown referenced 56) extending out of the page: the plane of the sheet of light 54 and the line of sight, referenced 58, of the window 46 are substantially perpendicular.

The relative positions of the mirror 40 and the detection window 46 are fixed, thus avoiding the need for separate careful control of their relative positions and orientations. They move together automatically when the shaft 38 is moved angularly (e.g. about its own axis). Furthermore, the endoscope 32 is small in comparison with prior art two-probe PIV systems.

Figure 6:
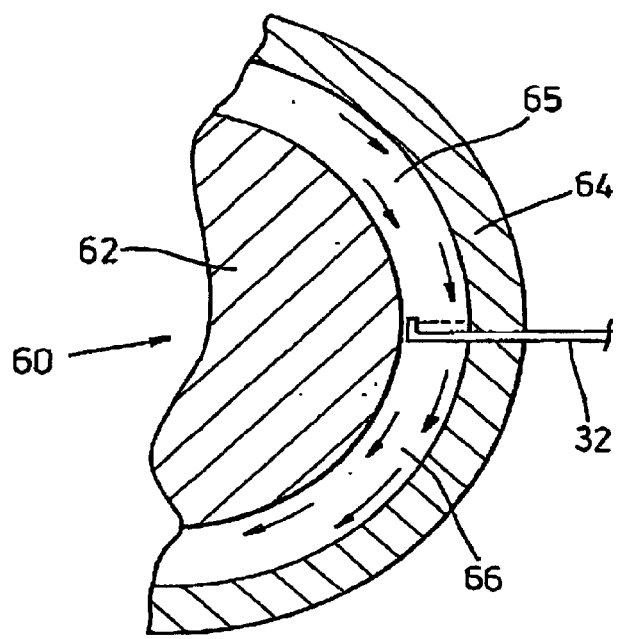
FIG. 6 shows the probe of FIG. 2 in use in an aircraft engine.

FIG. 6 shows the probe of FIG. 2 in use in a bearing 60 of an aircraft engine. The bearing has a first part 62 and a second part 64 separated by a gap 65 of 9 or 10 mm. The two parts 62 and 64 have a relative rotation of 10,000 rpm and are separated by a lubricating and cooling fluid 66 (typically oil). It is important to know that the oil 66 is not going to get too hot in use (or else there is a risk of engine fires), and that it does not get too much metal debris in it in too short a time.

The PIV sensor 32 is shown extending into the gap 65. By using thermal sensors, for example at the distal end of the endoscopic probe (or possibly somewhere else), the temperature of the oil can be determined in real time whilst the engine is operating.

Similarly, particle sizing techniques can be performed to assess the concentration and size of oil particles. It will be appreciated that it is better to have just one probe in the flow of oil, rather than two. It will also be appreciated that as well as being envisaged as test equipment for testing engines, the probe 32 (or a similar device) could be fitted to engines in use and could continuously or periodically report to an on-board controller/computer to monitor engine lubrication/cooling fluid whilst an aircraft is flying/operational. This can help to identify problems before they are critical, and help to take remedial action as appropriate.

We prefer to have a 4 mm diameter laser beam entering the sheet former 44. This, rather than narrower beams, is found at present to produce a better quality sheet. We also prefer to have the fibre optic 38 with a 4 mm diameter. It may be desirable to degrade the quality of the sheet of laser light in exchange for reduced diameter in certain applications.

Reflecting the sheet of light off mirror 40 increases the width of the sheet, whilst maintaining the probe relatively small.

Figure 3A:
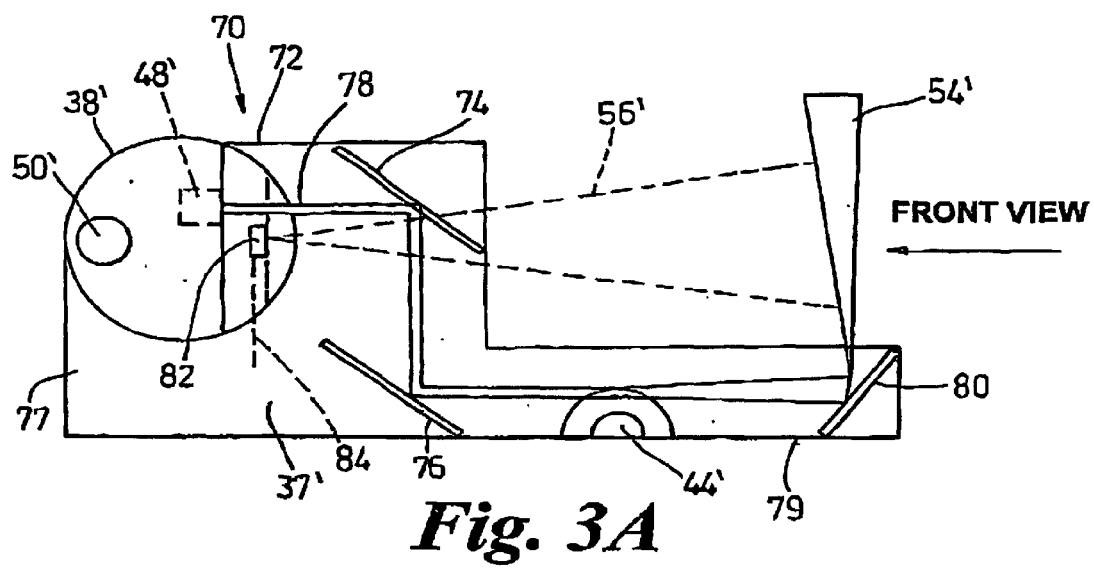
FIG. 3a shows a top view of a second probe design.
Figure 3B:
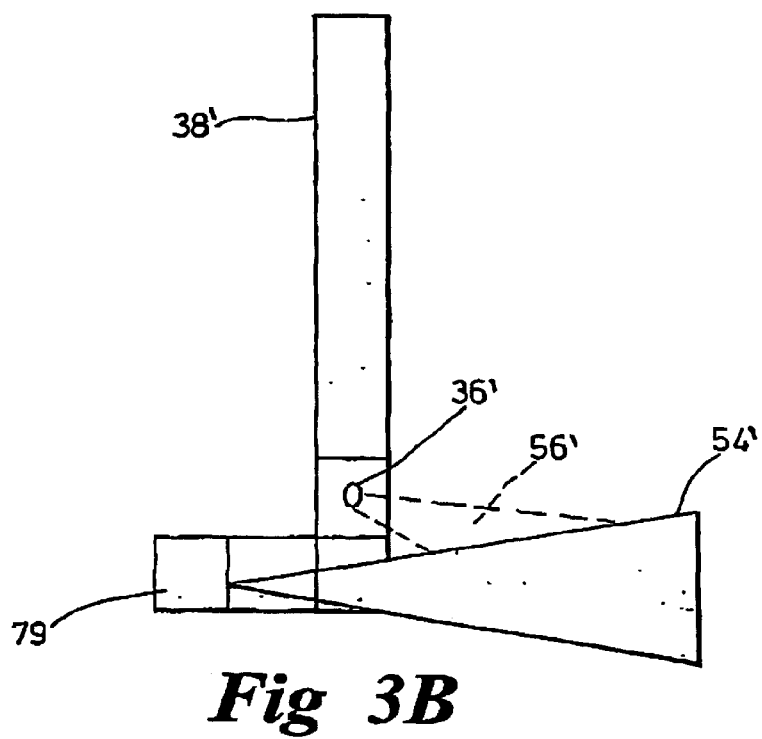
FIG. 3b shows a front view of the second probe design.

FIGS. 3a and 3b show a second design of endoscopic fluid-measuring probe adapted for measurement in a different shape of cavity. Components similar to those of FIG. 2 are given similar reference numerals.

The probe, referenced 70, has a longitudinal tubular shaft or borescope 38' extending perpendicularly from a base position 37'. A fibre optic 50' (which could be a bundle of fibres) extends longitudinally within borescope 38' and communicates with a light output unit 48' provided above base portion 37'. The base portion 37' is substantially L-shaped, with the borescope extending from corner 72. The base portion is provided with a set of parallel mirrors 74',76' set at 45° to the beam 78 of light emitted by the unit 48', one mirror being at each end of the short side (referenced 77) of the L-shaped base portion from which the borescope 38' extends.

A further mirror 80 is provided at the end of the long side (referenced 74) of the L-shaped base portion at an angle of 45° but perpendicular to the direction of the set of mirrors 74,76. A sheet forming optics 44' is positioned on the long side 79 of the L-shaped base portion 48 between the perpendicularly directed mirrors 74,76.

A prism is provided in the borescope at the viewing window 36' and comprises a swing prism 82 allowing the field of view to be moved to cover the complete area illuminated by the laser beam. The swing prism 82 pivots, as viewed in FIG. 3a, about axis 84, so as to pivot its central plane of view (referenced 56') through the plane of the page of drawings, above and below the page, depending upon its angular position.

In use the second probe design works in a similar manner to the first probe 32 design but the laser beam produced at the exit of the fibre optic bundle (at unit 46') is deflected by mirrors 74,76 to sheet forming optics 44', the resulting sheet is further deflected by mirror 80 to extend parallel to the short side of base portion 37'. The field of view of the image/data capturing mechanism at the window 36' is in addition movable to allow viewing analysis of the whole area illuminated by the laser sheet 21.

It will be appreciated that the embodiment of FIG. 2 could have a swing, or angularly movable, prism at its viewing window 46. This would give, in combination with rotating/angularly moving the shaft 38 a substantially all-angle field of view (as has the embodiment of FIGS. 3a and 3b).

Figure 4:
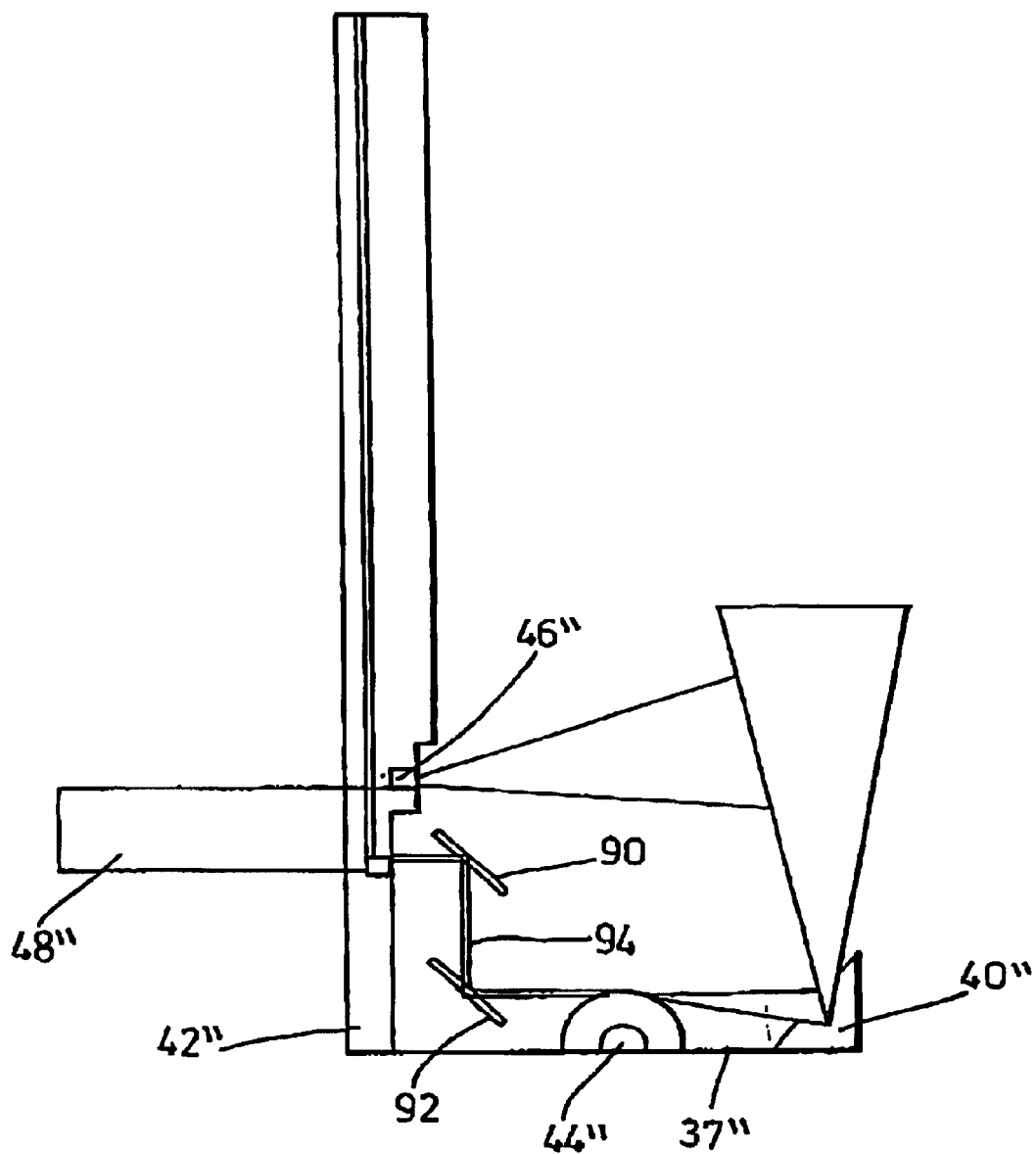
FIG. 4 shows a cross section of a third probe design.

FIG. 4 shows a modification of FIG. 2 wherein like features are given like numerals. In the borescope of FIG. 4 the end of the fibre optic bundle and its connection to the light output unit 48" is raised further above the base portion 37" than in FIG. 2, as is data capture window 46".

A mirror 90 is provided at 45° to the horizontal and level with the unit 48". A further mirror 92 as provided parallel to and beneath mirror 22.

The laser beam, referenced 94, is therefore deflected twice through 90° before contacting the sheet forming optics 44". By extending the distance between the viewing window and the sheet generation optics, the viewing area or measurement area is increased. It is anticipated that the fibre optics technology shall develop to allow transmission of high energy pulsed beams and in this case the mirrors may not be necessary.

Figure 5:
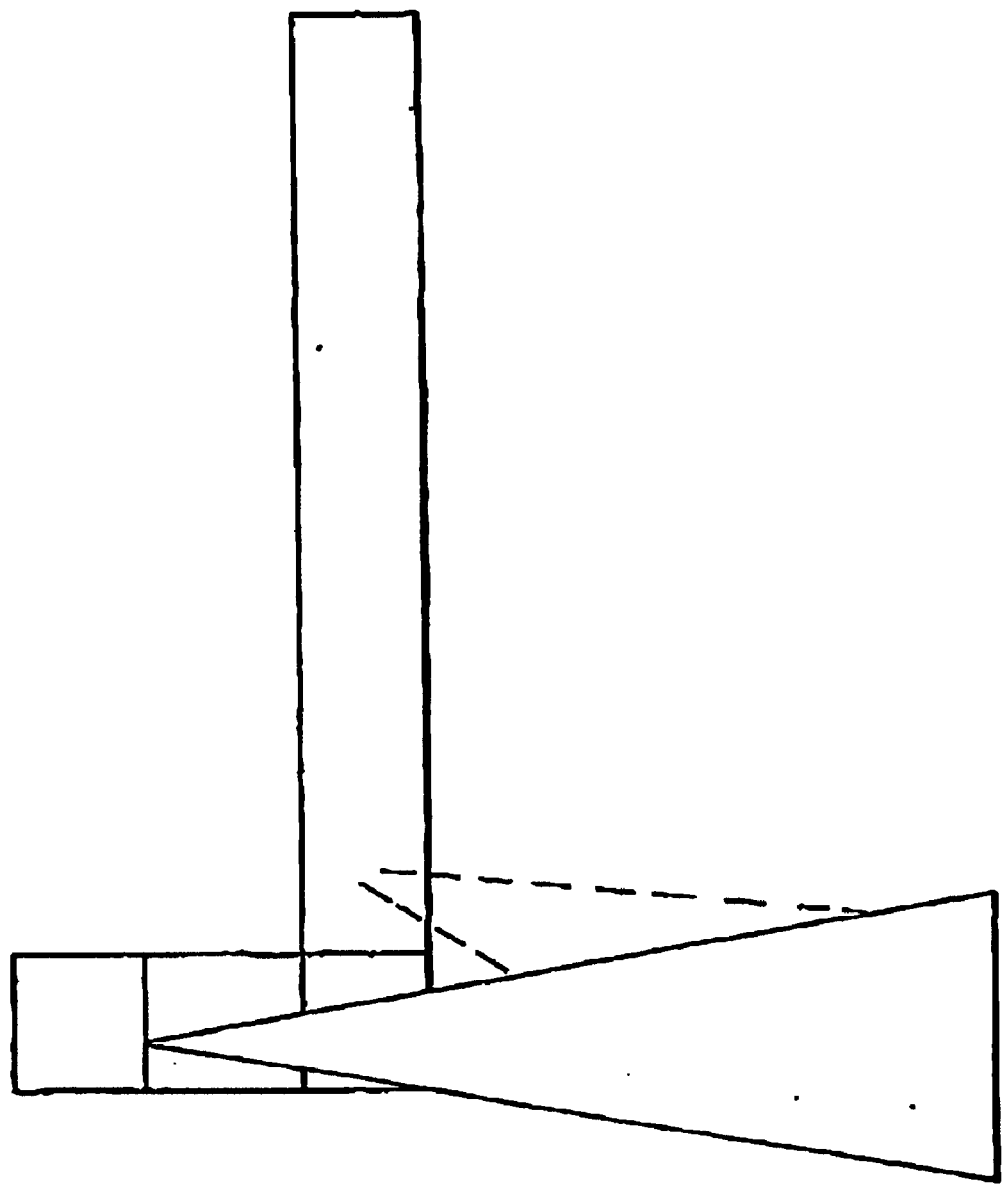
FIG. 5 shows a cross section of a fourth probe design.

The embodiment shown in FIG. 5 is very similar to the embodiment of FIGS. 3a and 3b and therefore like numerals indicate like features. The difference between the embodiment of FIG. 3 and that of FIG. 5 is the position of the swing prism in the embodiment of FIG. 4 is lower down the borescope. This is particularly needed when the annular geometry of a bearing chamber cannot accommodate other probe configurations.

As well as, or instead of, being used to generate PIV data (velocity of particles in a fluid, and hence the velocity of the fluid), the endoscopic probe can be used to measure particle size, particle size distribution, particle concentration, particle size concentration, temperature (thermal sensors), temperature distribution (e.g. using a thermal camera), LIF, and indeed other techniques where optically captured signals are required. It is especially suited to PLSA techniques, or LSV (Laser Sheet Visualisation) techniques.

The case of a single probe that both emits and receives light produces less disruption of flow and can get into smaller spaces than an emitter probe and separate receiver probe system. Moreover, the orientation and spacing of the emitter/receiver can be preset, and move together since they are both mounted on the same carrier. The probe may be provided with movable output and/or receive components, whose movement may be controlled by a control computer (e.g. electrically via motors). We may use incoherent light, so long as we can create 2-D sheets of captured light for PIV (when that is the technique being used). The device in many embodiments operates in real time (depending upon the processing power available), and if it has real time sensors/CCD camera.

Other areas of application include the medical field, where blood flow in blood vessels (e.g. brain or heart arteries or veins) can be measured.

Figure 7:
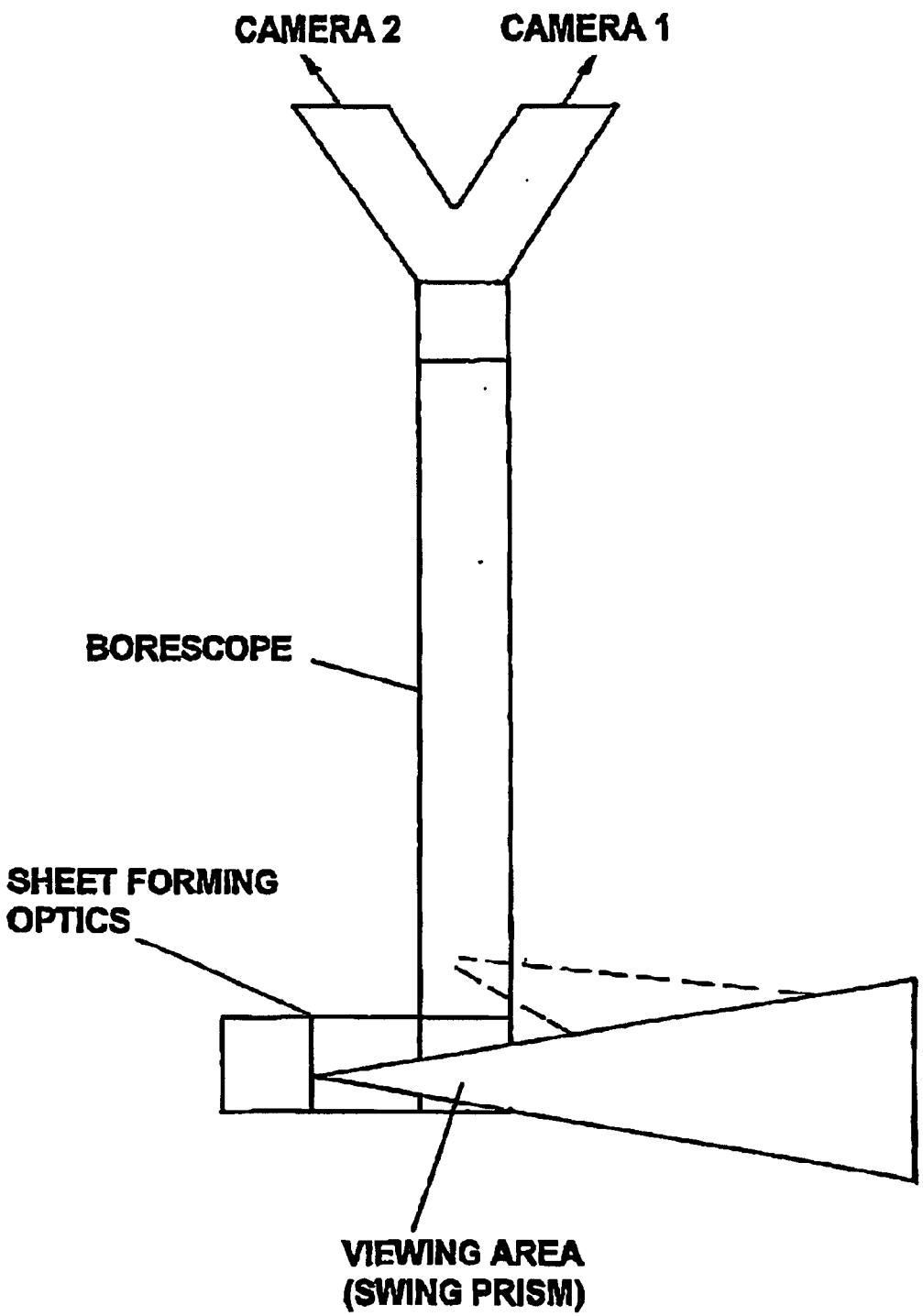
FIG. 7 shows a fifth probe design.

FIG. 7 shows another version of the probe, this time having two cameras. These can be used to observe in different wavelengths simultaneously and/or sequentially.

Figure 8:
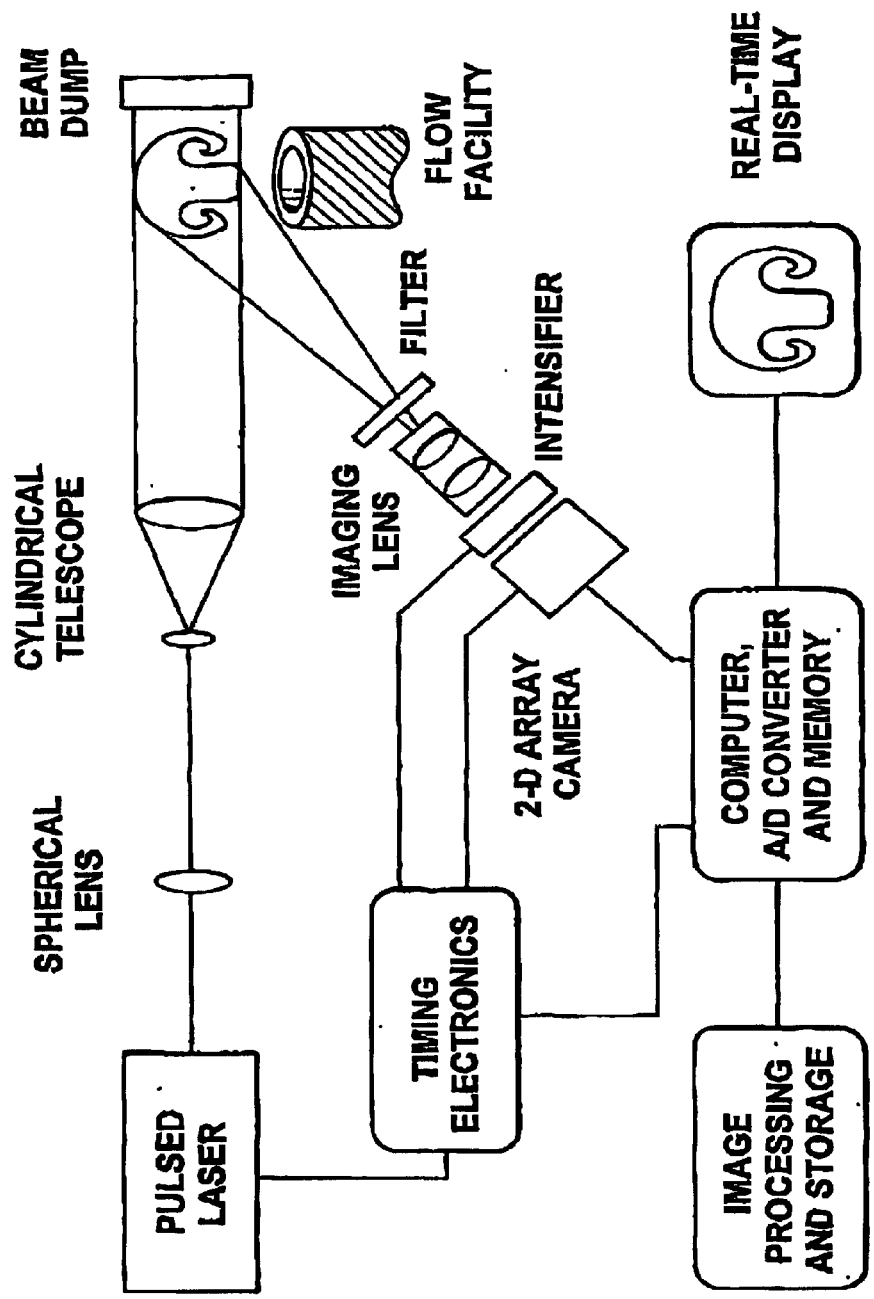
FIG. 8 shows a prior art technique of PLIF (Pulsed Laser Induced Fluorescence)

The general arrangement for PLIF imaging is shown in FIG. 8. A laser source, usually pulsed and tuneable in wavelength, is used to form a thin sheet of light which traverses the flow field under study. If the laser wavelength is resonant with an optical transition of a species present in the flow, a fraction of the incident photons will be absorbed at each point within the illumination plane. A fraction of these absorbed photons may subsequently be re-emitted with a modified spectral distribution, which changes for different molecules and varies with flow field conditions. The emitted photons, known as "fluorescence", may be viewed as a form of molecular scattering and constitute the signal of interest in PLIF imaging. The fluorescence intensity distribution of the illumination plane recorded by the camera essentially provides an image of the product of absorber number density in a particular quantum state and the local fluorescence yield, i.e. the fraction of absorbed light converted to fluorescence. By various strategies, this signal can be related to other flowfield properties of interest. The temporal resolution of the measurement in atmospheric (and higher) pressure combustion is effectively controlled by the laser source, with 5–20 ns pulse lengths being typical. The greatest achievable spatial resolution of the image is set by the sensor array, which may contain from 10 000 to more than 1 million pixels.

Fluorescence imaging may be viewed as a modern form of flow visualisation. In common with methods such as schlieren and shadowgraphy, PLIF is extremely useful for qualitative characterisation of complex flow fields, but it has the important added capabilities of species-specificity and of providing spatially resolved information in a plane rather than integrated over a line-of-sight. The former characteristic is critical for studies of reacting flows, while the latter quality is important for resolving three-dimensional flow field structure.

Figure 9A:
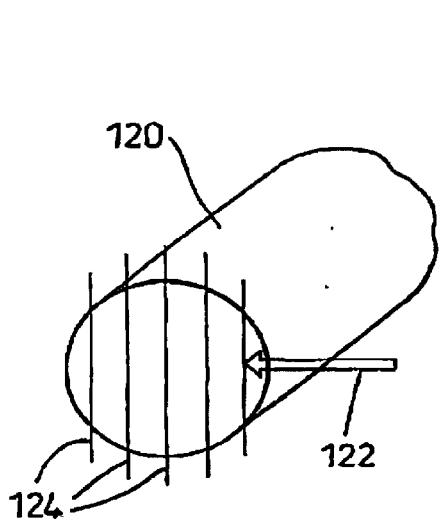
FIGS. 9a and 9b show the use of a probe to measure flow in a pipe.
Figure 9B:
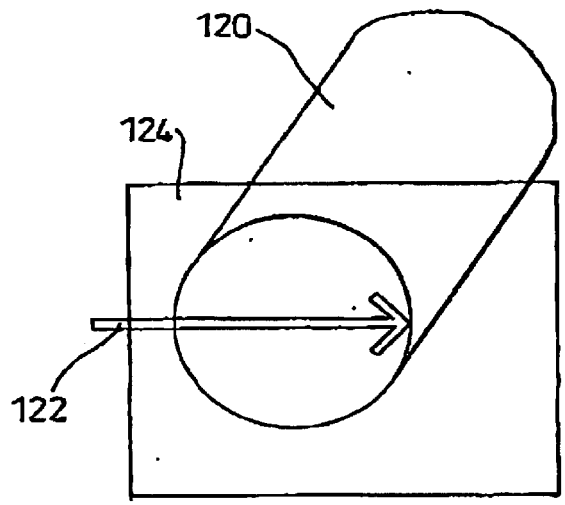
Figure 9:
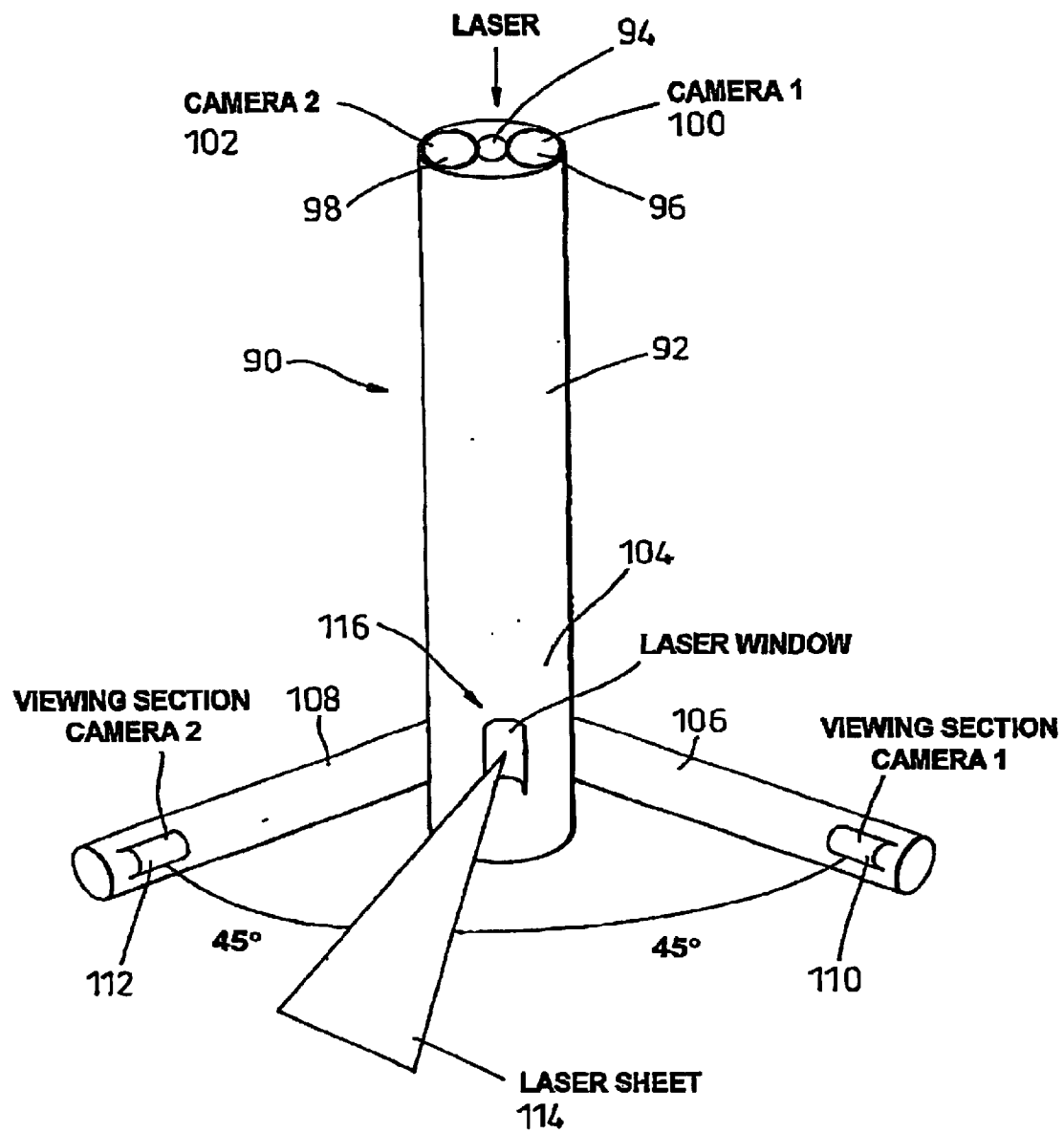
FIG. 9 shows a further embodiment of the invention.

FIG. 9 shows another embodiment. An endoscopic probe 90 has a main elongate shaft 92 which is much longer than it is wide and which contains a laser transmission channel 94, extending from a laser (not shown), and first and second acquired/captured image channels 96 and 98 leading to respective cameras 100 and 102. The distal end, referenced 104, of the probe has two arms 106 and 108 fixed to the shaft 92 (in a fixed relationship with the part of the shaft 92 that they engage). The arms 106 and 108 have viewing windows/image acquiring areas 110 and 112 adapted to image a light sheet (referenced 114). The light sheet 114 is produced in use by a light sheet producer 116 provided at the distal end 104, coupled to the laser transmission channel 94.

The light sheet 114 is in the plane coming out of the page of FIG. 9, at an angle equidistant from arms 106 and 108 (which are at 90° to each other), that is to say at 45° to the plane of the light sheet 114. The sheet 114 passes between the viewing windows 110 and 112 and they view the sheet substantially perpendicularly. This is achieved by having reflectors (not shown) in the viewing windows that are substantially parallel to the plane of the sheet 114.

As will be understood, a particle in the plane of the light sheet can be viewed from either side of the sheet as it moves and the out-of-plane velocity of the particle can be established. This can be important in some applications.

As an example, FIGS. 9a and 9b show a pipe 120 and an endoscopic probe 122 being used to measure the flow along the pipe, across its cross-sectional area. FIG. 9a shows a probe with only one image acquirer which can measure in-plane velocities being used to measure the velocity at different places across the cross-section of a pipe in order to establish a flow velocity profile over the cross-sectional area of the pipe. This involves several measurements.

FIG. 9b shows a stereoscopic probe being used to establish the flow velocity profile over the cross-section of the pipe with fewer re-positionings of the probe (only one position, or perhaps two) because it can acquire out-of-plane velocities. The light sheets are referenced 124.

Figure 10:
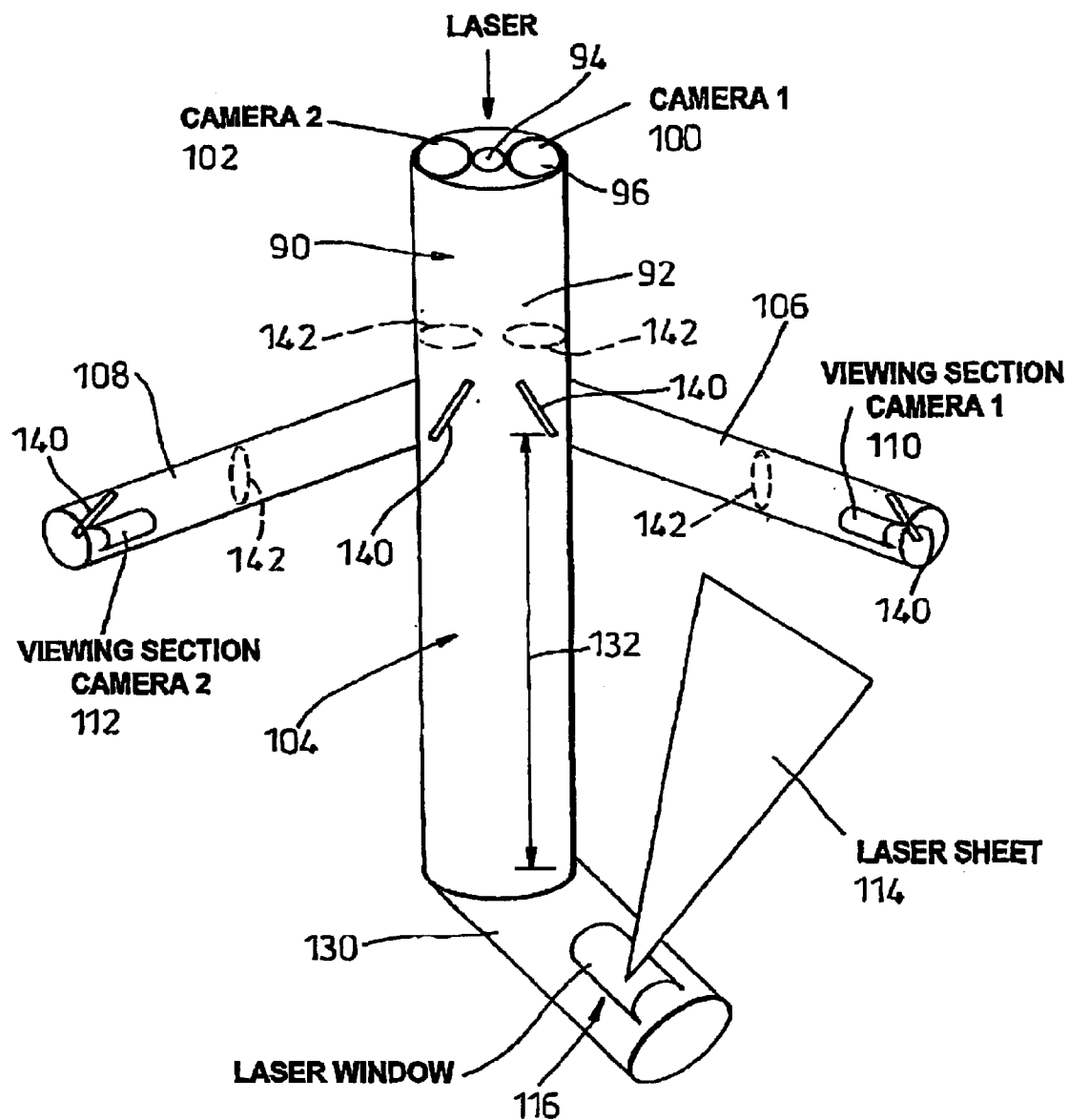
FIG. 10 shows another embodiment of the invention.

FIG. 10 shows another stereoscopic laser light sheet probe that is similar to that of FIG. 9, but with a different configuration. Similar components have been given similar reference numbers to those used in FIG. 9. The probe 90 has a foot 130 in which is provided the light sheet generator 116, the foot 130 extends away from the shaft 92 at right angles. The light sheet is generated in a "vertical" plane that is parallel to, or generally parallel to, the elongate direction of the shaft 92. The distance in the elongate direction of the shaft 92 between the arms 106, 108 and the foot 116, distance referenced 132 in FIG. 10, determines how wide the laser sheet has spread, and therefore the size of area viewed by the image acquirers 110 and 112. If a larger area of plane is to be viewed the arrangement of FIG. 10 makes this possible without having to increase the length of the arms 106,108 (which would need to be done for the arrangement of FIG. 9).

The probe projects a laser sheet in the flow area under scrutiny and acquires two images of the flow field viewed from opposite sides of the sheet. The viewing angle for each image acquirer in this example is 45° (and is preferably equal for each image acquirer even if the angle is not 45°). This overcomes an alignment problem usually associated with stereoscopic 3-D PIV in that although the acquirer arm is set at 45° to the light sheet the image acquirer views the sheet at 90°, with the image in focus, because of the realignment of the image acquirer's first image-capture mirror to be parallel to the light sheet.

FIG. 10 also schematically shows mirrors 140 and beam conditioning lenses 142.

Figure 11:
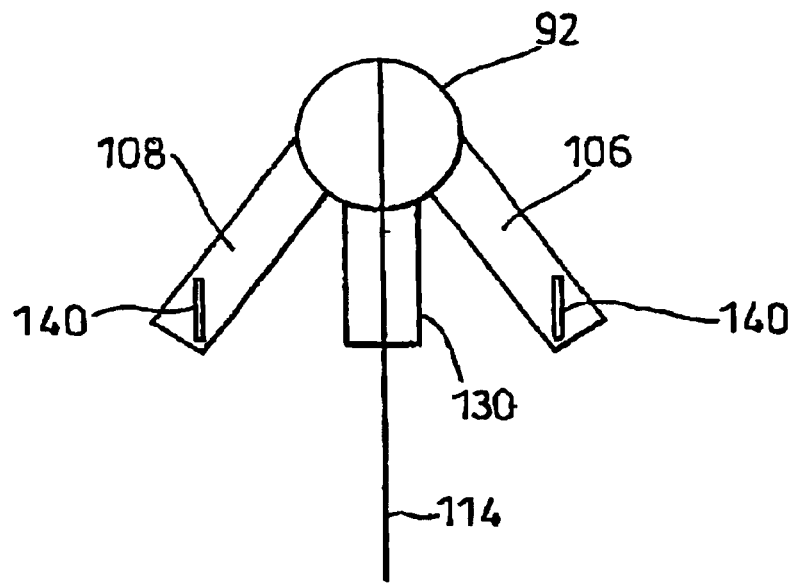
FIGS. 11 and 12 show modifications of the embodiments.

FIG. 11 shows schematically the alignment of the image-acquiring mirrors 140 of the embodiment of FIG. 10 (and FIG. 9) with the plane of the light sheet so as to have the light sheet in the same focal plane.

Figure 12:
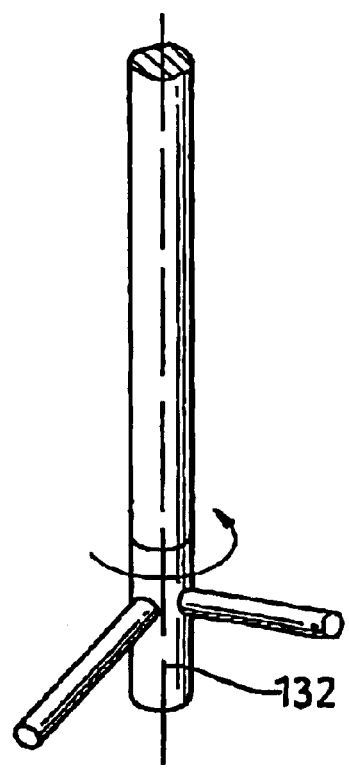

FIG. 12 shows a modification of the previous embodiments. Previously the endoscope has been in a fixed, preset, configuration. In FIG. 12, the distal end containing the sheet-producing and image acquiring optics is still in a preset fixed relationship, but the distal end referenced 132 is angularly movable, in this example about the axis of the shaft of the probe. In other examples it could be angularly movable about a different axis.

The arm(s) could be movable relative to the shaft. For example, they could fold in to assist insertion of the probe through a hole and then fold out for use. The arm(s) or foot could be movable along the axial length of the shaft. The axial spacing between the light sheet emitter and image capturer(s) could be adjustable.

Whilst systems with one or two cameras have been described, it may be desirable to have more than two cameras.

Figure 13:
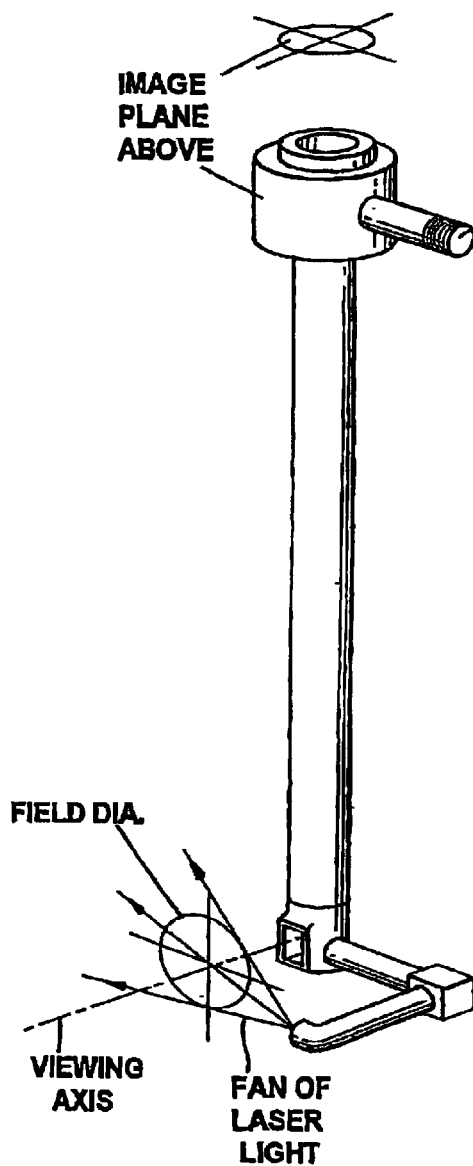
FIGS. 13 and 14 show two more embodiments.

FIG. 13 shows a prototype endoscopic PLS probe with a dog-leg arrangement to present a fan of light in front of a viewing window provided at the bottom of the main axial column or rod of the probe, with the viewing window and sheet of light emitter being at generally the same position along the axial length of the probe.

Figure 14:
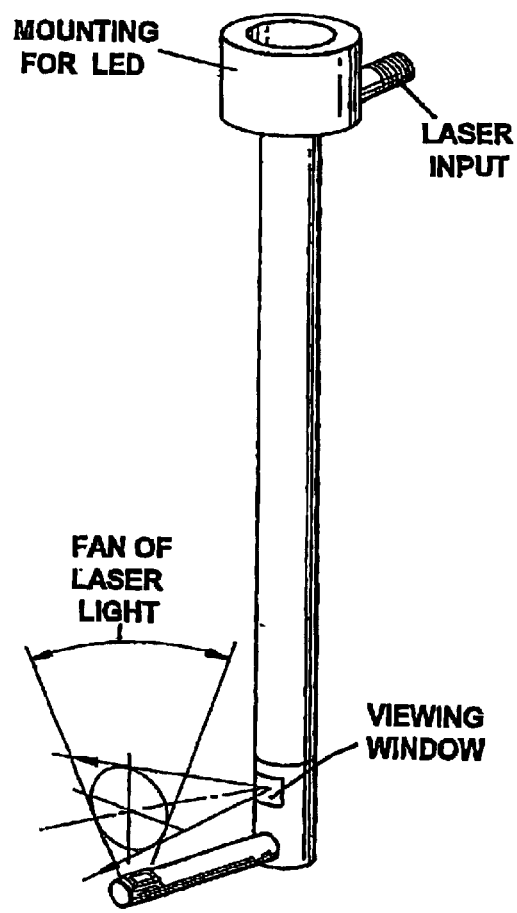

FIG. 14 shows another arrangement in which the viewing window is displaced axially from the position of the sheet of light emitter.

The main advantages of the probe of the present invention are:

LSV, PIV, LIF and PLSA stereoscopic 3-D PIV visualisations and measurements made possible in enclosed cavities.

This one piece probe, combining the transmission and receiving optics in the same stem, can be used from miniature to large scale applications.

Measurements are possible wherever an endoscope can be used.

3 dimensional experimental tests can be performed.

Truly non-intrusive and semi intrusive measurement can be performed.

Any enclosed cavity with only one small access is needed.

Miniature to big area size PIV can be performed.

Very efficient and less costly.

Perfect setting (No setting of the light sheet and the camera is required inside the engine).

Tests can be performed on a real rig. Thus, more accurate results and cost effective.

For the different settings or designs of the instrument, a basic instrument can be developed with different optical attachments or accessories An endostereoscopic probe has advantages.

In addition to having applications in aircraft engines, where it is used to scrutinise the fluid flow events in the hostile and conventionally inaccessible environment, the technology has applications in other engineering disciplines; particularly in turbomachinery. For example, the levels of combustion (e.g. probe in the exhaust pipe); qualities/parameters in the exhaust and/or intake/fuel manifold, and/or fuel injection system; viewing/measuring reactions in any engine regardless of the fuel it burns, and in flow analysis in pipes, and/or particle distribution/particle characterisation of particles suspended in a flowing fluid (e.g. in pipes).

By "light" we mean to cover any electromagnetic wave.

What is claimed is:

1. An optical endoscopic fluid flow measurement probe assembly comprising an endoscope having a user end and a distal end, the distal end having a light sheet generator and at least one reflected light acquirer, and the endoscope being provided with transmission means to transmit information away from the distal end, the light sheet generator being adapted in use to generate a sheet of light having a side face and the light acquirer being adapted to detect light reflected from the light sheet, the light sheet generator and light acquirer being provided in the same endoscope and wherein the reflected light acquirer is disposed relative to the light sheet generator so as to have a line of sight transverse to the plane of the sheet of light that is produced by the light sheet generator, so that the reflected light acquirer looks onto the side face of the light sheet in use.

2. A probe according to claim 1 which comprises a LSV, PIV, LIF, PLSA, or stereoscopic 3-D PIV probe, and in which the light sheet generator comprises a laser light sheet generator adapted to produce a sheet of laser light, and in which the light acquirer comprises an imager adapted to capture an image from the light sheet.

3. A probe according to claim 1 wherein the light emitter is closer to the distal end than is the light acquirer.

4. A probe according to claim 1 wherein the light acquirer is optically coupled to image transmission optics adapted to transmit an optical image or signal detected by the light acquirer away from the distal end to the user end of the probe.

5. A probe according to claim 1, which comprises a fibre optic, or fibre optic bundle, extending along its length and optically coupled to the light emitter.

6. A probe according to claim 1, which has at least two light acquirers and which comprises a stereoscopic probe.

7. A probe according to claim 1 wherein the transmission optics comprise one or more of lenses, prisms, mirrors, and light sheet generators.

8. A probe according to claim 1 wherein the endoscope has an elongate tubular body provided with an extension at or towards its distal end extending away from the body, the extension being provided with on of the light emitter or light acquirer, and in which the other of the light emitter or light acquirer is provided at the body at a different position along the axial length of the body.

9. A probe according to claim 1 wherein the light emitter and light acquirer are disposed at generally the same position along the axial length of an elongate body of the probe.

10. A probe according to claim 1 wherein the light emitted by the light emitter is arranged to propagate in a plane that contains a line generally parallel to the elongate direction of the body.

11. A probe according to claim 10 wherein a reflector is mounted on a carrier and is moveable about a first axis, and in which the carrier is itself angularly movable about a second, different, axis.

12. A probe according to claim 1 wherein the or each light acquirer has a reflective surface that is generally parallel to the plane in which the light sheet will be produced by the light sheet generator.

13. A fluid flow analyser system comprising a probe according to claim 1 coupled to a light source, and coupled to a camera or other detector.

14. A system according to claim 13 wherein the light source comprises a laser.

15. A system according to claim 14 comprising a control device which in use controls the operation of the laser and receives signals from the detector and in which the control device is also adapted, in use, to control the movement of the endoscope.

16. A method of determining a parameter associated with a fluid in a restricted space and/or a hostile environment, comprising using an endoscopic optical probe having an elongate length and provided with an optical light emitting element towards its distal end and provided with an optical light acquiring element towards its distal end, the probe being adapted to emit a sheet of light via the light emitting element and to collect light via the light acquiring element that has been emitted by the emitting element and interacted with the fluid; and transferring acquired light along the endoscopic probe to a remote sensor, remote from the distal end of the endoscopic probe; and processing signals produced by the remote sensor to evaluate a parameter of the fluid; creating a sheet of light using the probe; imaging at least part of the sheet of light using the probe and applying one of the following techniques to the signals obtained: Laser Sheet Visualisation, Particle Image Velocimetry; Laser Induced Fluorescence; Planar Light Sheet Anemometry; Stereoscopic 3-D PIV.

17. A method according to claim 16 used to determine at least one of the following in an engine bearing: fluid flow; particle analysis; temperature.

18. A method according to claim 16 wherein a laser is used to produce the light sheet, and in which the light sheet is transmitted into the fluid, or confined space or cavity, using fibre optics.

19. A method of performing LSV, PIV, LIF, PLSA, or stereoscopic 3-D PIV, or other optical fluid flow analytic techniques, comprising using the same endoscope to emit a sheet of light and to image reflected light by means of at least one image acquirer provided on the endoscope.

20. A method according to claim 19 in which there are two image acquirers on the endoscope.

21. An optical endoscopic fluid flow measurement probe assembly comprising an endoscope having a user end and a distal end, the distal end having a light sheet generator and at least one reflected light acquirer, the light sheet generator being adapted in use to generate a sheet of light and the light acquirer being disposed spaced from the light sheet generator so as to view a side surface of the sheet light and being adapted to detect light reflected from the light sheet, the light sheet generator and light acquirer being provided in the same endoscope, and wherein the probe is from the group:

LSV, PIV, LIE, PLSA, or stereoscopic 3-D PW probe;

and wherein the light sheet generator comprises a laser light sheet generator adapted to produce a sheet of laser light, and in which the light acquirer comprises an imager adapted to capture an image from the light sheet.

22. An optical endoscopic fluid flow measurement probe assembly comprising an endoscope having a user end and a distal end, the distal end having a light sheet generator and at least one reflected light acquirer, the light sheet generator being adapted in use to generate a sheet of light and the light acquirer being adapted to detect light reflected from the light sheet, the light sheet generator and light acquirer being provided in the same endoscope, and wherein the probe is from the group:

LSV, PIV, LIF, PLSA, or stereoscopic 3-D PIV probe;

and wherein the light sheet generator comprises a laser light sheet generator adapted to produce a sheet of laser light, and in which the light acquirer comprises an imager adapted to capture an image from the light sheet;

and wherein the sheet generator is closer to the distal end than is the light acquirer and wherein the light sheet generator is adapted to generate a sheet of light that extends transversely relative to a line of sight of the light acquiring, which line of sight intersects the light sheet in use;

and the light acquirer is optically coupled to image transmission optics adapted to transmit an optical image or signal detected by the light acquirer away from the distal end to the user end of the probe;

and which further comprises a fibre optic, or fibre optic bundle, extending along its length and optically coupled to the light emitter.

23. An optical endoscopic fluid flow measurement probe assembly comprising an endoscope having a user end and a distal end, the distal end having a light sheet generator and at least one reflected light acquirer, the light sheet generator being adapted in use to generate a sheet of light and the light acquirer being adapted to detect light reflected from the light sheet, the light sheet generator and light acquirer being provided in the same endoscope, and wherein the probe is from the group:

LSV, PIV, LIF, PLSA, or stereoscopic 3-D PIV probe;

and wherein the light sheet generator comprises a laser light sheet generator adapted to produce a sheet of laser light, and in which the light acquirer comprises an imager adapted to capture an image from the light sheet;

and wherein said probe has at least two light acquirers and comprises a stereoscopic probe.

24. An optical endoscopic fluid flow measurement probe assembly comprising an endoscope having a user end and a distal end, the distal end having a light sheet generator and at least one reflected light acquirer, the light sheet generator being adapted in use to generate a sheet of light and the light acquirer being adapted to detect light reflected from the light sheet, the light sheet generator and light acquirer being provided in the same endoscope, and wherein the probe is from the group:

LSV, PIV, LIF, PLSA, or stereoscopic 3-D PIV probe;

and wherein the light sheet generator comprises a laser light sheet generator adapted to produce a sheet of laser light, and in which the light acquirer comprises an imager adapted to capture an image from the light sheet;

and wherein the endoscope has an elongate tubular body provided with an extension at or towards its distal end extending away from the body, the extension being provided with one of the light emitter or light acquirer, and in which the other of the light emitter or light acquirer is provided at the body at a different position along the axial length of the body;

and wherein the light emitted by the light emitter is arranged to propagate in a plane that contains a line generally parallel to the elongate direction of the body;

and wherein a reflector is mounted on a carrier and is movable about a first axis, and in which the carrier is itself angularly movable about a second, different, axis.

25. A probe according to claim 24 wherein the or each light acquirer has a reflective surface that is generally parallel to the plane in which the light sheet will be produced by the light sheet generator.

26. A method of determining a parameter associated with a fluid in a restricted space and/or a hostile environment, comprising using an endoscopic optical probe having an elongate length and provided with an optical light emitting element towards its distal end and provided with an optical light acquiring element towards its distal end, the probe being adapted to emit a sheet of light via the light emitting element and to collect light via the light acquiring element that has been emitted by the emitting element and interacted with the fluid; and transferring acquired light along the endoscopic probe to a remote sensor, remote from the distal end of the endoscopic probe; and processing signals produced by the remote sensor to evaluate a parameter of the fluid; creating a sheet of light using the probe; imaging at least part of the sheet of light using the probe and applying one of the following techniques to the signals obtained: Laser Sheet Visualisation, Particle Image Velocimetry; Laser Induced Fluorescence; Planar Light Sheet Anemometry; Stereoscopic 3-D PIV; wherein a laser is used to produce the light sheet, and in which the light sheet is transmitted into the fluid, or confined space or cavity, using fiber optics, and further comprising using the same endoscope to emit a sheet of light and to image reflected light by means of at least one image acquirer provided on the endoscope.

27. An optical endoscopic fluid flow measurement probe assembly comprising an endoscope having a user end and a distal end, the distal end having a light sheet generator and at least one reflected light acquirer, and the endoscope being provided with transmission means to transmit information away from the distal end, the light sheet generator being adapted in use to generate a sheet of light having a side face and the light acquirer being adapted to detect light reflected from the light sheet, the light sheet generator and light acquirer being provided in the same endoscope and wherein the reflected light acquirer is disposed relative to the light sheet generator so as to have a line of sight transverse to the plane of the sheet of light that is produced by the light sheet generator, so that the reflected light acquirer looks onto the side face of the light sheet in use; and a control computer coupled to said probe assembly for processing signals produced therefrom to evaluate a parameter of the fluid; image at least part of the sheet of light using the probe and applying one of the following techniques to the signals obtained: Laser Sheet Visualisation, Particle Image Velocimetry; Laser Induced Fluorescence; Planar Light Sheet Anemometry; Stereoscopic 3-D PIV.

* * * * *